United States Patent
McGuckin, Jr.

(10) Patent No.: US 9,095,449 B2
(45) Date of Patent: Aug. 4, 2015

(54) METHOD OF INSERTING A SPINAL IMPLANT

(75) Inventor: James F. McGuckin, Jr., Radnor, PA (US)

(73) Assignee: Rex Medical, L. P., Conshohocken, PA (US)

(*) Notice: Subject to any disclaimer, the term of this patent is extended or adjusted under 35 U.S.C. 154(b) by 1020 days.

(21) Appl. No.: 11/821,300

(22) Filed: Jun. 22, 2007

(65) Prior Publication Data
US 2008/0009944 A1    Jan. 10, 2008

Related U.S. Application Data

(62) Division of application No. 10/253,446, filed on Sep. 24, 2002, now Pat. No. 7,267,687.

(60) Provisional application No. 60/326,438, filed on Oct. 2, 2001.

(51) Int. Cl.
| | | |
|---|---|---|
| A61F 2/44 | (2006.01) | |
| A61F 2/46 | (2006.01) | |
| A61B 17/70 | (2006.01) | |
| A61B 17/00 | (2006.01) | |
| A61B 17/02 | (2006.01) | |
| A61F 2/30 | (2006.01) | |

(52) U.S. Cl.
CPC ............ *A61F 2/4611* (2013.01); *A61B 17/70* (2013.01); *A61F 2/442* (2013.01); *A61B 2017/00261* (2013.01); *A61B 2017/00557* (2013.01); *A61B 2017/00867* (2013.01); *A61B 2017/0256* (2013.01); *A61F 2002/30092* (2013.01); *A61F 2002/444* (2013.01); *A61F 2002/4627* (2013.01); *A61F 2210/0014* (2013.01)

(58) Field of Classification Search
CPC ....... A61F 2/446; A61F 2/442; A61F 2/4611; A61F 2002/444; A61F 2210/0014; A61B 17/7002; A61B 17/7031; A61B 17/702; A61B 2017/00867
USPC ................ 623/17.11, 17.12, 17.16, 1.18–1.2
See application file for complete search history.

(56) References Cited

U.S. PATENT DOCUMENTS

| | | |
|---|---|---|
| 3,867,728 A | 2/1975 | Kahn et al. |
| 4,904,261 A | 2/1990 | Dove et al. |
| 5,578,074 A * | 11/1996 | Mirigian ...................... 606/108 |
| 5,716,416 A | 2/1998 | Lin |

(Continued)

FOREIGN PATENT DOCUMENTS

| | | |
|---|---|---|
| DE | 19710392 C1 | 7/1999 |
| DE | 2006 005868 | 6/2006 |

(Continued)

*Primary Examiner* — Brian Pellegrino
(74) *Attorney, Agent, or Firm* — Neil D. Gershon

(57) ABSTRACT

A spinal implant having a smaller transverse cross-sectional dimension in the radially compressed configuration than in a first expanded configuration and a more linear configuration in the second delivery configuration than in the first curved configuration. The implant assumes the radially compressed configuration and second delivery configuration during delivery to the disc space and assumes the first curved configuration and first expanded configuration upon placement within the disc space. The implant further moves towards the radially compressed configuration once implanted in response to a load placed on the implant by the vertebral bodies.

12 Claims, 13 Drawing Sheets

(56) References Cited

U.S. PATENT DOCUMENTS

| | | |
|---|---|---|
| 5,749,916 A | 5/1998 | Richelsoph |
| 5,800,549 A | 9/1998 | Bao et al. |
| 5,824,093 A | 10/1998 | Ray et al. |
| 5,830,222 A * | 11/1998 | Makower ................ 606/159 |
| 5,879,385 A | 3/1999 | Crockard et al. |
| 5,919,235 A | 7/1999 | Baumgartner et al. |
| 5,976,187 A | 11/1999 | Richelsoph |
| 6,117,174 A | 9/2000 | Nolan |
| 6,127,597 A | 10/2000 | Beyat et al. |
| 6,132,465 A | 10/2000 | Ray et al. |
| 6,143,031 A | 11/2000 | Knothe et al. |
| 6,165,218 A | 12/2000 | Husson et al. |
| 6,179,875 B1 | 1/2001 | Von Strempel |
| 6,206,923 B1 | 3/2001 | Boyd et al. |
| 6,224,630 B1 | 5/2001 | Bao et al. |
| 6,245,108 B1 | 6/2001 | Biscup |
| 6,264,695 B1 | 7/2001 | Stoy |
| 6,280,475 B1 | 8/2001 | Bao et al. |
| 6,306,170 B2 | 10/2001 | Ray |
| 6,315,797 B1 | 11/2001 | Middleton |
| 6,387,130 B1 | 5/2002 | Stone et al. |
| 6,395,031 B1 * | 5/2002 | Foley et al. ............. 623/17.11 |
| 6,402,785 B1 | 6/2002 | Zdeblick et al. |
| 6,419,705 B1 | 7/2002 | Erickson |
| 6,432,107 B1 | 8/2002 | Ferree |
| 6,500,178 B2 | 12/2002 | Zucherman et al. |
| 6,508,839 B1 | 1/2003 | Lambrechet et al. |
| 6,582,468 B1 | 6/2003 | Gauchet |
| 6,592,624 B1 | 7/2003 | Fraser et al. |
| 6,592,625 B2 | 7/2003 | Cauthen |
| 6,607,557 B1 | 8/2003 | Brosnahan et al. |
| 6,607,558 B2 | 8/2003 | Kuras |
| 6,610,094 B2 | 8/2003 | Husson |
| 6,613,089 B1 | 9/2003 | Estes et al. |
| 6,613,090 B2 | 9/2003 | Fuss et al. |
| 6,613,091 B1 | 9/2003 | Zdeblick et al. |
| 6,626,943 B2 | 9/2003 | Eberlein et al. |
| 6,645,248 B2 | 11/2003 | Casutt |
| 6,648,915 B2 | 11/2003 | Sazy |
| 6,656,224 B2 | 12/2003 | Middleton |
| 6,669,732 B2 | 12/2003 | Serhan et al. |
| 6,805,695 B2 | 10/2004 | Keith et al. |
| 7,018,413 B2 | 3/2006 | Kruger |
| 7,182,783 B2 | 2/2007 | Trieu |
| 7,267,690 B2 | 9/2007 | Felt |
| 7,351,262 B2 | 4/2008 | Bindseil et al. |
| 7,442,210 B2 | 10/2008 | Segal et al. |
| 7,491,219 B2 | 2/2009 | Steinberg |
| 7,591,853 B2 | 9/2009 | Felt et al. |
| 2001/0010021 A1 | 7/2001 | Boyd et al. |
| 2002/0026244 A1 | 2/2002 | Trieu |
| 2002/0077641 A1 | 6/2002 | Michelson |
| 2002/0077701 A1 | 6/2002 | Kuslich |
| 2002/0120269 A1 | 8/2002 | Lange |
| 2002/0173851 A1 | 11/2002 | McKay |
| 2003/0018390 A1 | 1/2003 | Husson |
| 2003/0093154 A1 | 5/2003 | Estes et al. |
| 2004/0220669 A1 | 11/2004 | Studer |
| 2004/0230309 A1 | 11/2004 | DiMauro et al. |
| 2005/0096745 A1 | 5/2005 | Andre et al. |
| 2005/0119747 A1 | 6/2005 | Fabris Monterumici et al. |
| 2005/0131541 A1 | 6/2005 | Trieu |
| 2006/0041258 A1 | 2/2006 | Galea |
| 2006/0085002 A1 | 4/2006 | Trieu et al. |
| 2006/0089646 A1 | 4/2006 | Bonutti |
| 2006/0106462 A1 | 5/2006 | Tsou |
| 2006/0173545 A1 | 8/2006 | Cauthen et al. |
| 2006/0189999 A1 | 8/2006 | Zwirkoski |
| 2006/0190083 A1 | 8/2006 | Arnin et al. |
| 2006/0247776 A1 | 11/2006 | Kim |
| 2006/0247781 A1 | 11/2006 | Francis |
| 2006/0247784 A1 | 11/2006 | Kim |
| 2006/0265077 A1 | 11/2006 | Zwirkoski |
| 2006/0287726 A1 | 12/2006 | Segal et al. |
| 2007/0010889 A1 | 1/2007 | Francis |
| 2007/0016298 A1 | 1/2007 | Recoules-Arche et al. |
| 2007/0055272 A1 | 3/2007 | Schaller |
| 2007/0067035 A1 | 3/2007 | Falahee |
| 2007/0150064 A1 | 6/2007 | Ruberte et al. |
| 2007/0162132 A1 | 7/2007 | Messerli |
| 2007/0191861 A1 | 8/2007 | Allard et al. |
| 2008/0039942 A1 | 2/2008 | Bergeron |
| 2008/0058933 A1 | 3/2008 | Garner et al. |
| 2008/0091269 A1 | 4/2008 | Zipnick et al. |
| 2008/0125865 A1 | 5/2008 | Abdelgany |
| 2008/0221687 A1 | 9/2008 | Viker |
| 2008/0243249 A1 | 10/2008 | Kohm et al. |
| 2008/0249628 A1 | 10/2008 | Altarac et al. |
| 2008/0312743 A1 | 12/2008 | Vila et al. |
| 2009/0030423 A1 | 1/2009 | Puno |
| 2009/0171389 A1 | 7/2009 | Sankaran |
| 2009/0182386 A1 | 7/2009 | Schaller |
| 2009/0248092 A1 | 10/2009 | Bellas et al. |
| 2009/0254180 A1 | 10/2009 | Pazanowski et al. |

FOREIGN PATENT DOCUMENTS

| | | | |
|---|---|---|---|
| EP | 1442715 | 8/2004 | |
| WO | WO 0106962 | 2/2001 | |
| WO | WO 0112107 A1 * | 2/2001 | ............... A61F 2/44 |
| WO | WO 0217824 | 3/2002 | |
| WO | 03011155 | 2/2003 | |

* cited by examiner

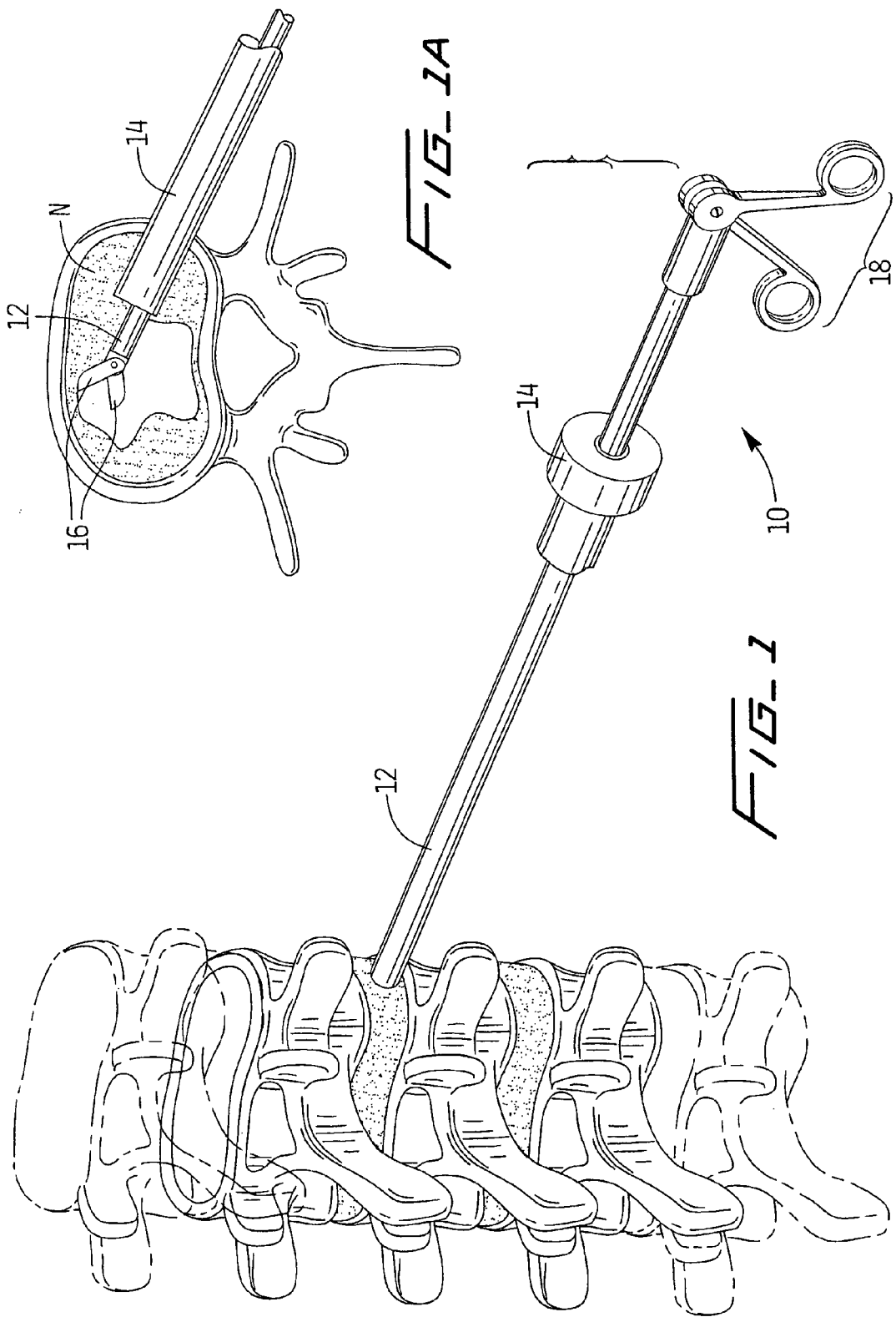

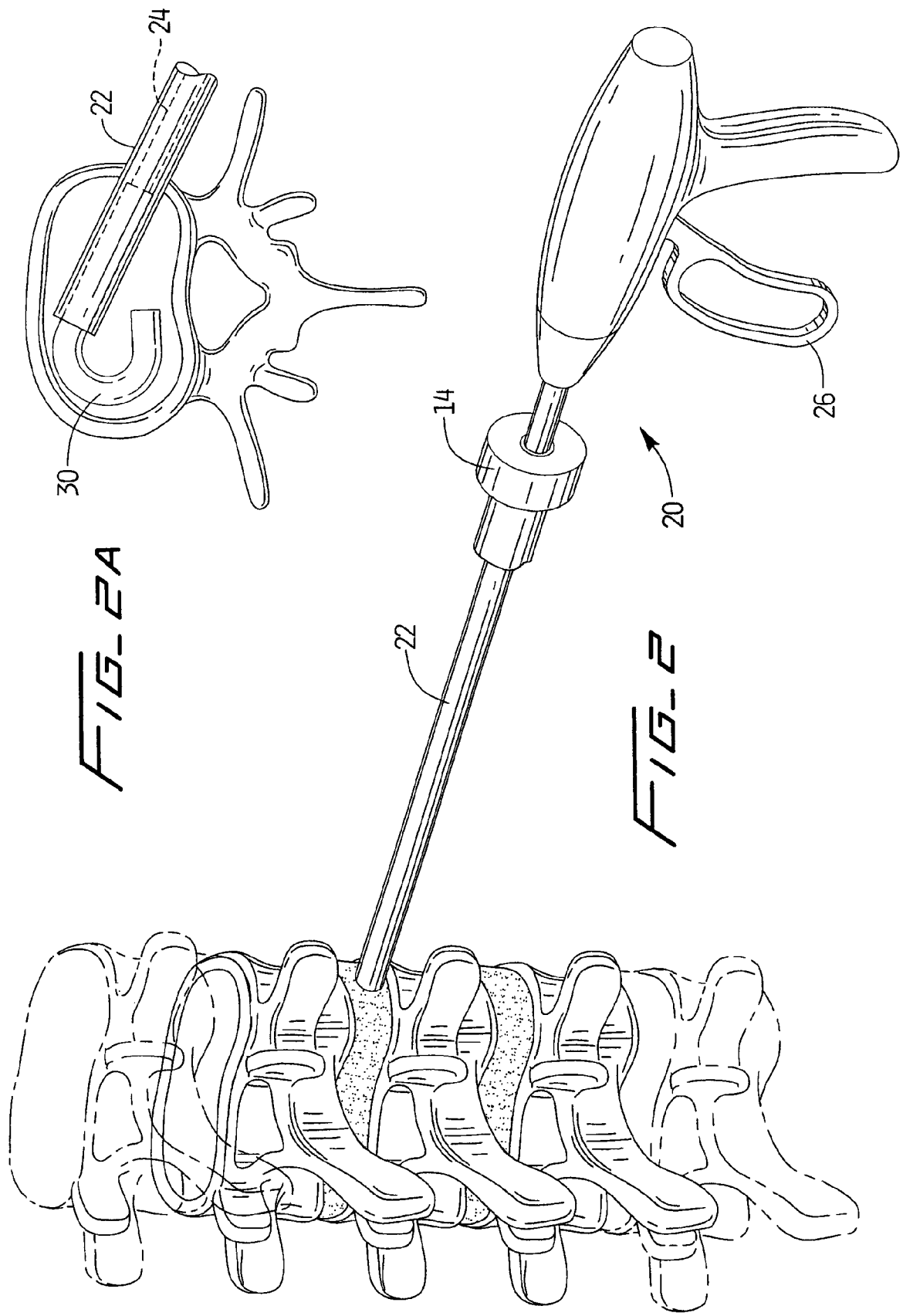

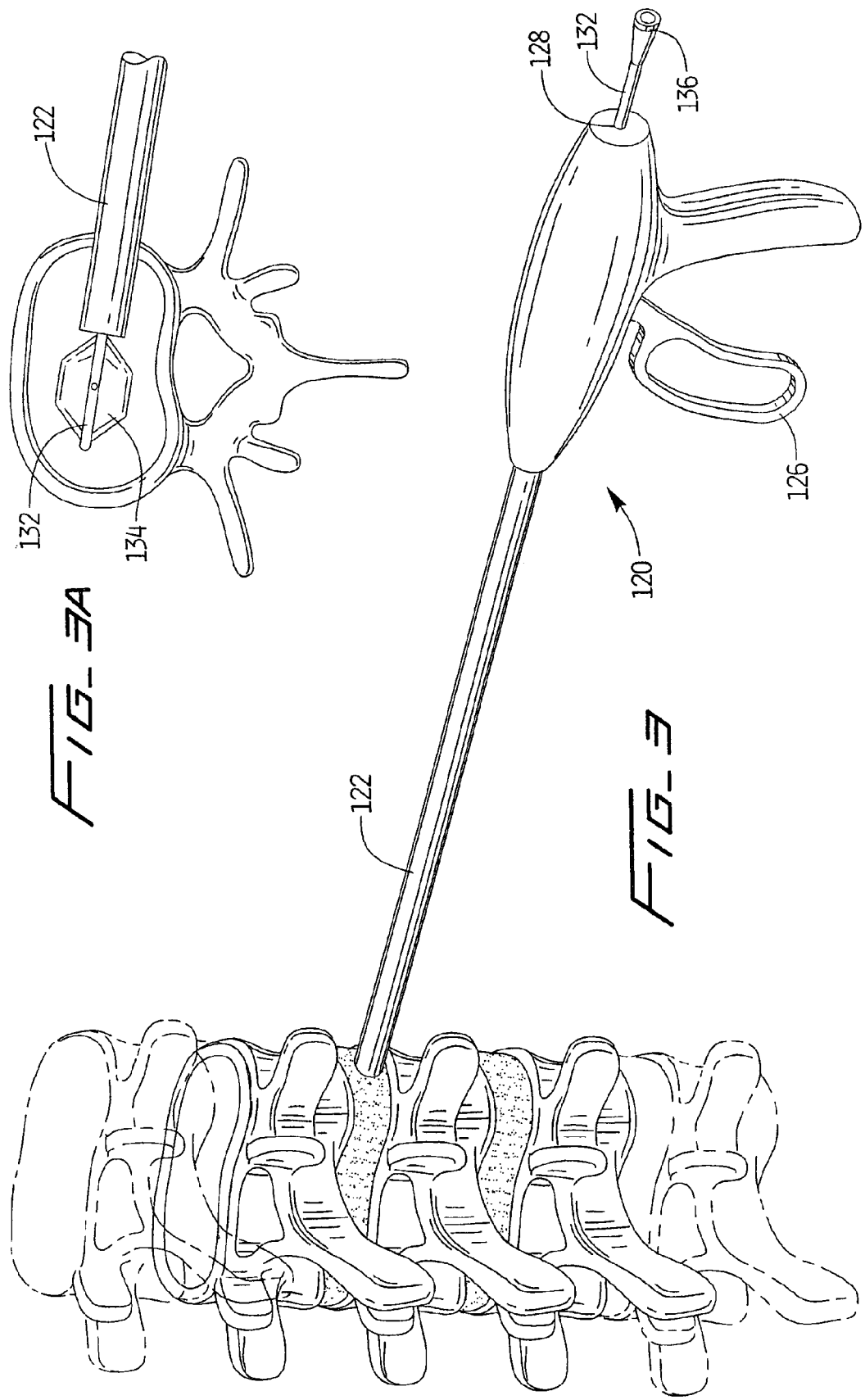

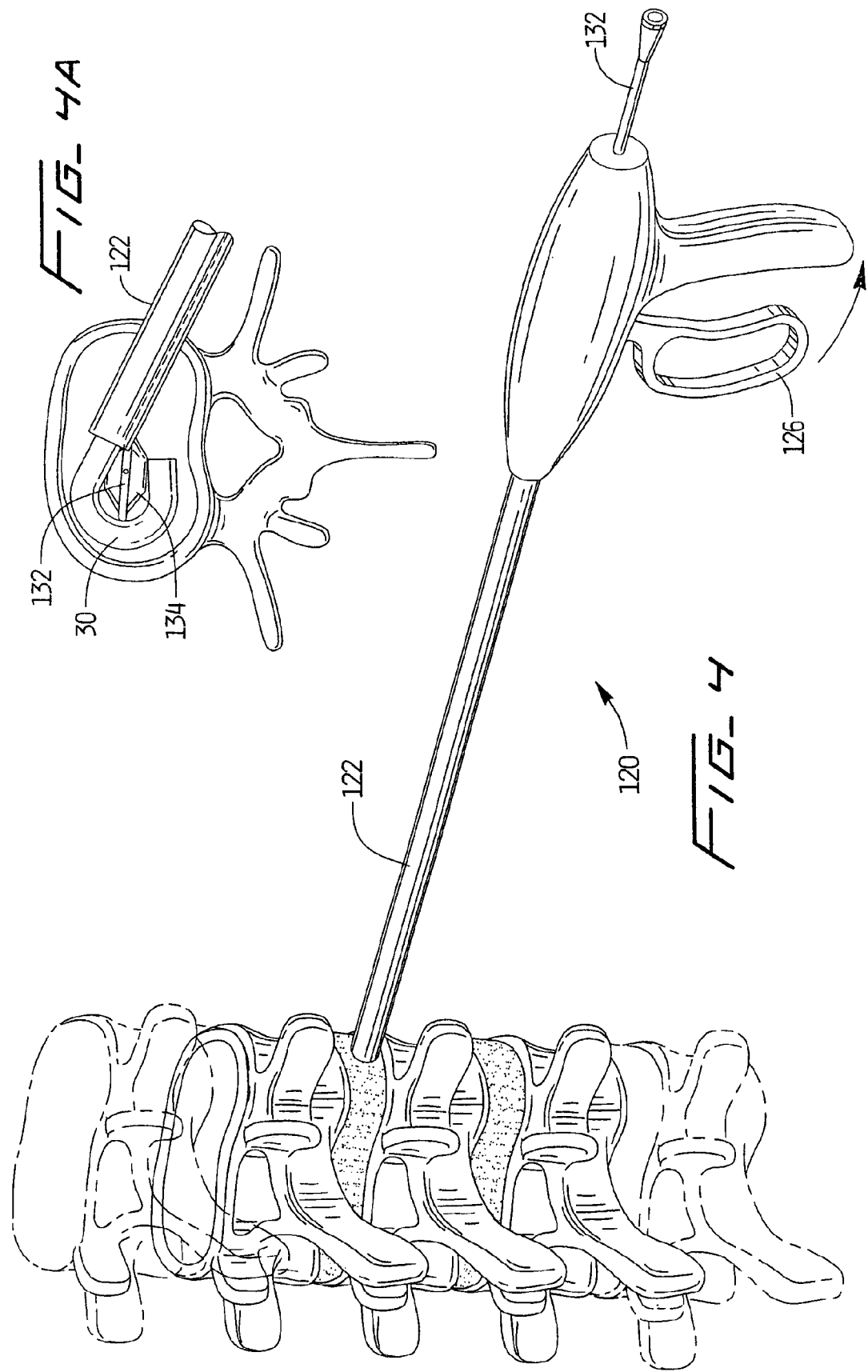

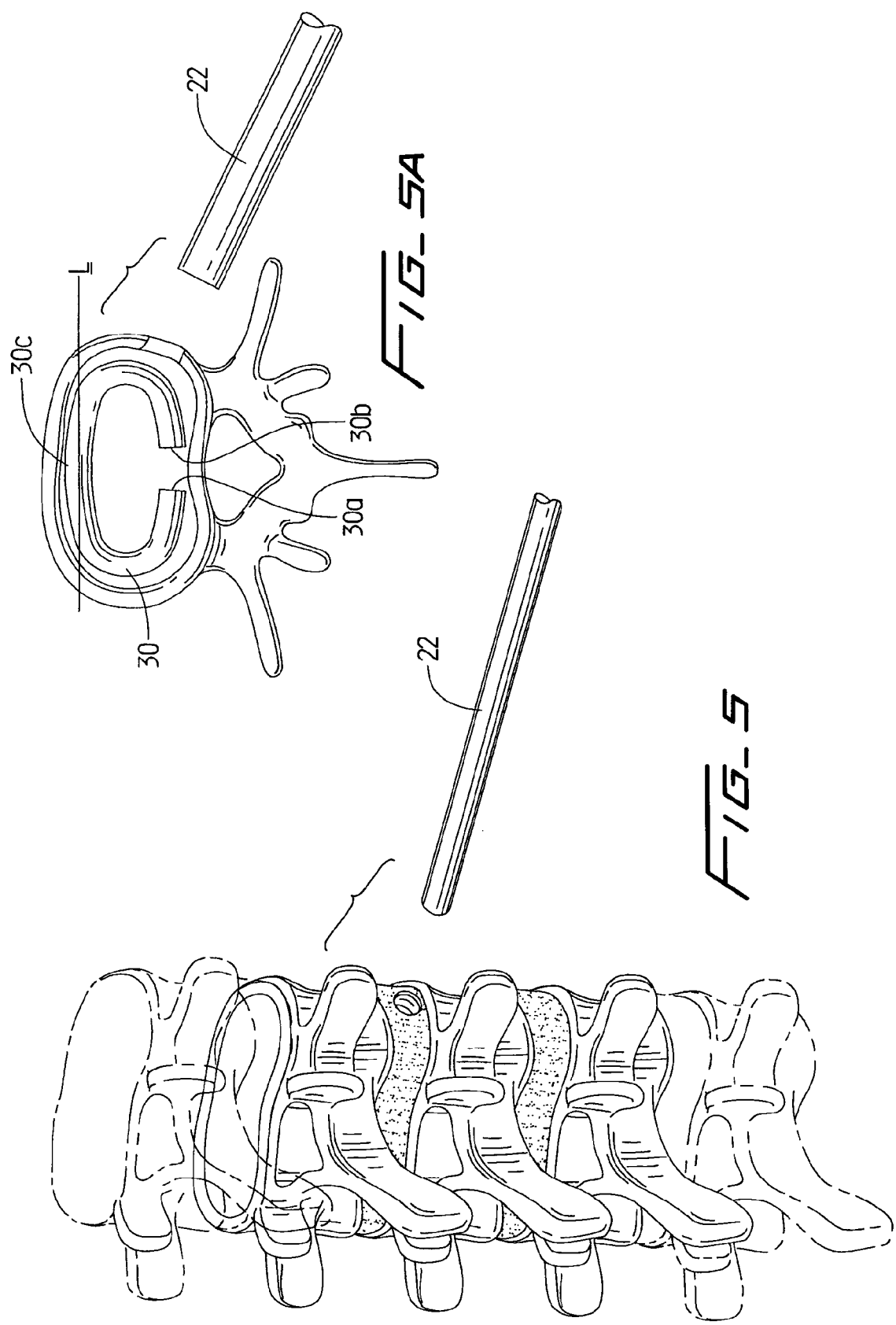

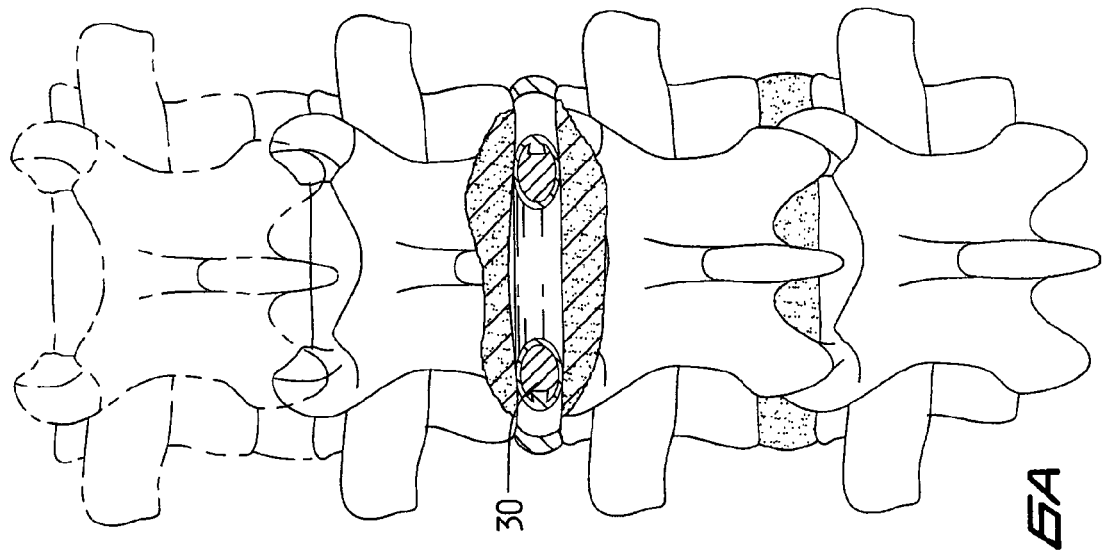
FIG._6
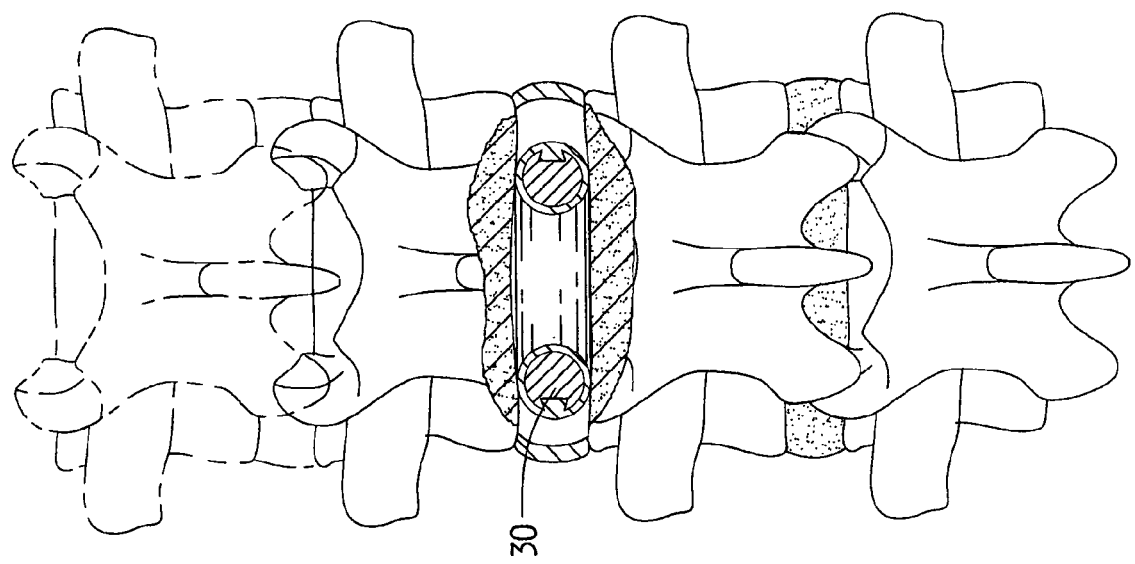
FIG._6A

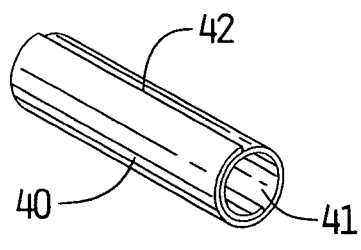
FIG_ 7
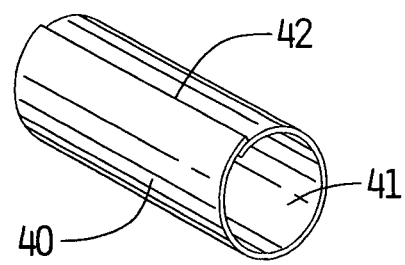
FIG_ 7A
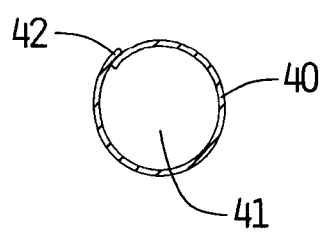
FIG_ 7B
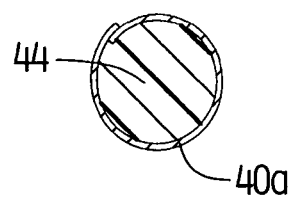
FIG_ 7C
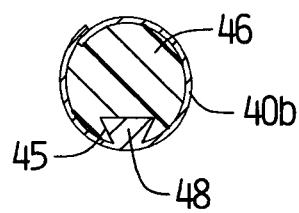
FIG_ 7D
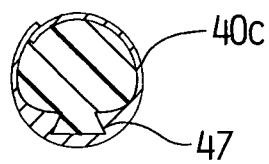
FIG_ 7E

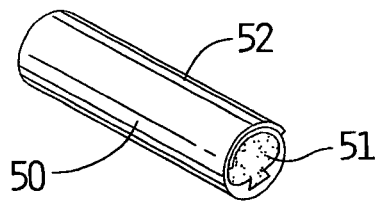
FIG_8
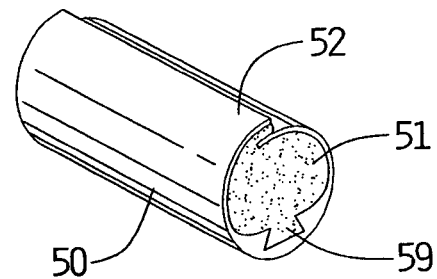
FIG_8A
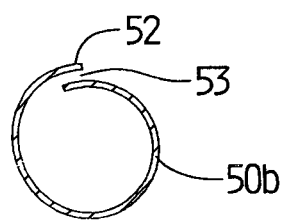
FIG_8B
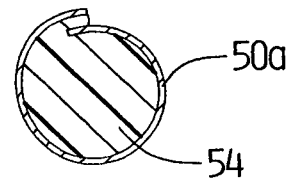
FIG_8C
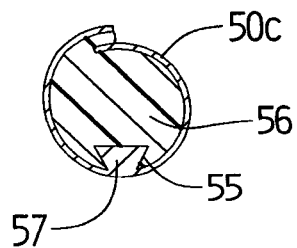
FIG_8D
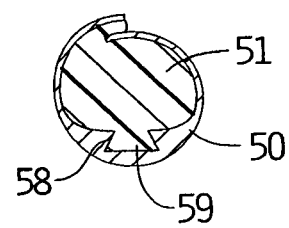
FIG_8E

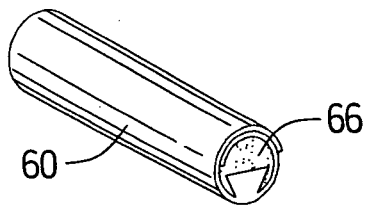
FIG_9
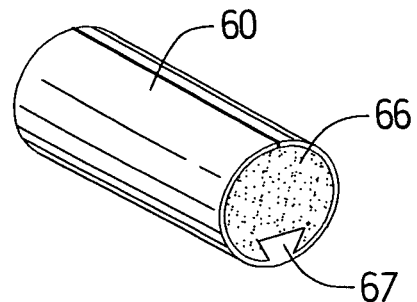
FIG_9A
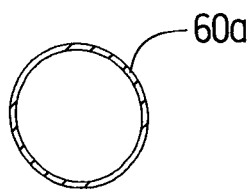
FIG_9B
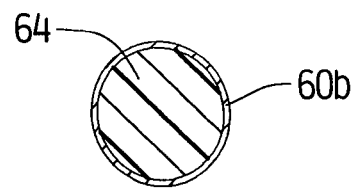
FIG_9C
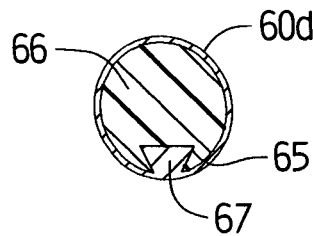
FIG_9D
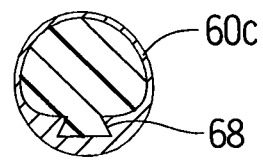
FIG_9E

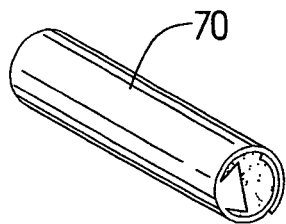
FIG_10
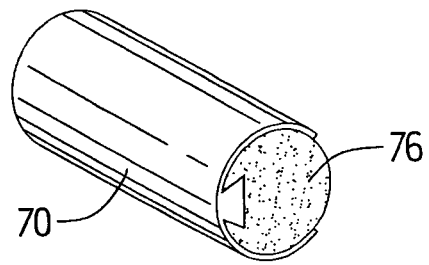
FIG_10A
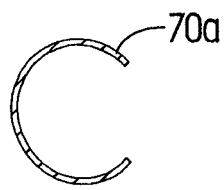
FIG_10B
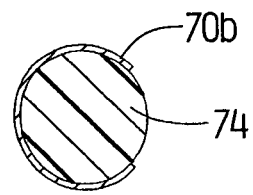
FIG_10C
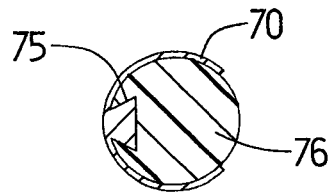
FIG_10D
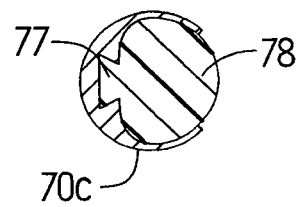
FIG_10E FIG_11
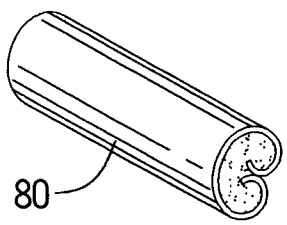
FIG_11A
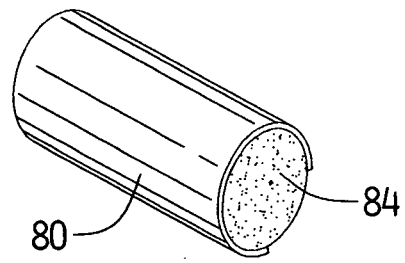
FIG_11B
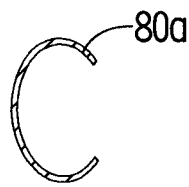
FIG_11C
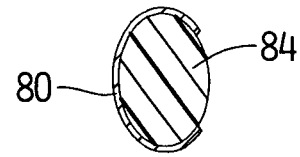
FIG_11D
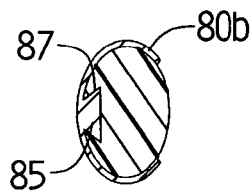
FIG_11E
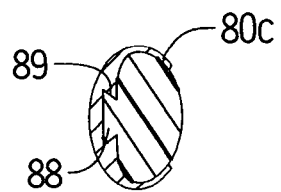

FIG_12
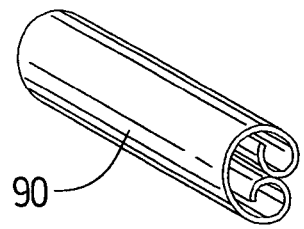
FIG_12A
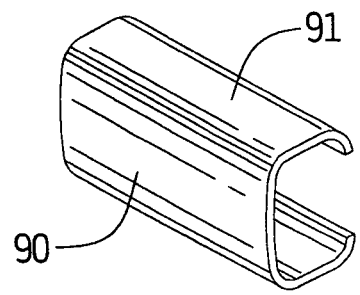
FIG_12B
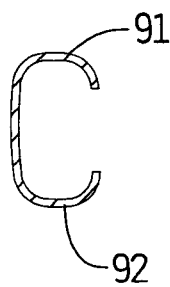
FIG_12C
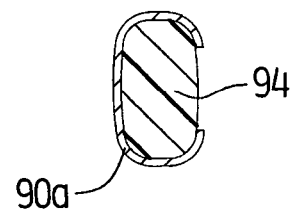
FIG_12D
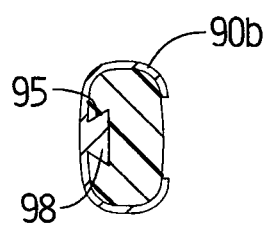
FIG_12E
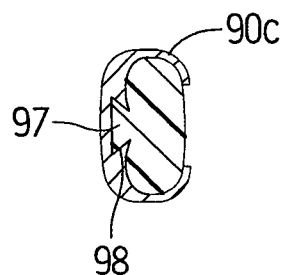

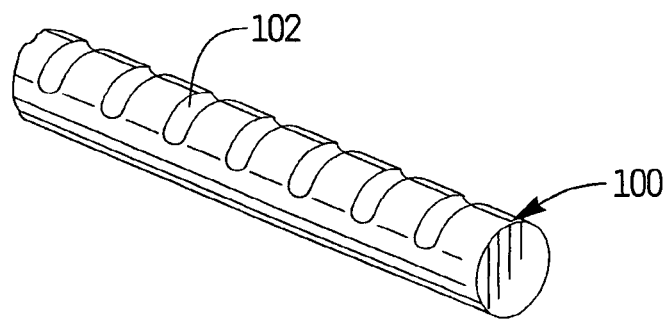
FIG_13
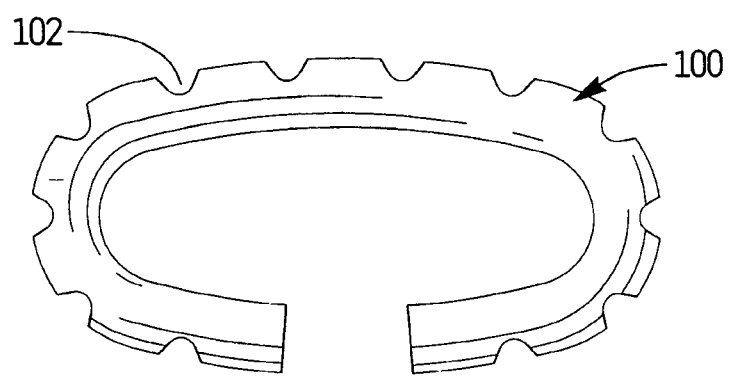
FIG_14
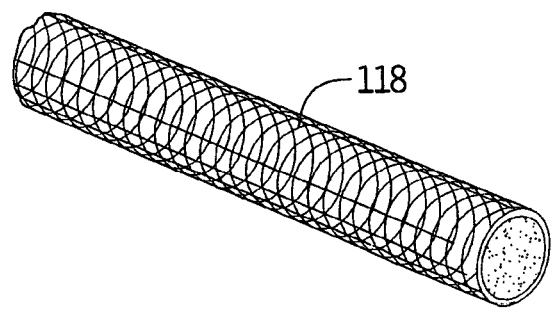
FIG_15

METHOD OF INSERTING A SPINAL IMPLANT

BACKGROUND

This application is a divisional of application Ser. No. 10/253,446, filed on Sep. 24, 2002 now U.S Pat. No. 7,267,687, which claims priority from provisional application Ser. No. 60/326,438, filed on Oct. 2, 2001. The entire contents of both applications are incorporated herein by reference.

TECHNICAL FIELD

This application relates to a spinal implant and more particularly to a spinal disc implant that can be inserted minimally invasively.

BACKGROUND OF RELATED ART

After removal of the intervertebral disc, it has been recognized that the disc space needs to be filled between the adjacent vertebrae. There are two approaches in the prior art to fill the space: one involving placement of a fusion cage and the other involving an artificial disc. Fusion cages are essentially metallic cages packed with bone to promote bone ingrowth. The fusion cages, designed to promote fusion, provide support between the vertebrae, but eliminate motion. Thus, to achieve stability, they sacrifice mobility.

Artificial disc prostheses of the prior art take many forms. Each form is essentially designed to strike a balance between sufficient stability to support the high loads of the vertebrae and sufficient mobility so as not to curtail movement of the patient. To date, attempts to strike such balance have met with limited success, with the artificial disc providing either stability or mobility, but not both. The need therefore exists for a disc replacement that can better simulate the natural disc by combining adequate support with flexibility.

Additionally, in many intervertebral procedures, major open surgery is required. The advantages of endoscopic (minimally invasive) procedures are well known, e.g. smaller incision causing less trauma and reduced infection potential, shorter hospital stays, lower costs, reduced patient recovery time, and reduced pain for the patient. Therefore, it would be advantageous if such an artificial disc, which achieves a beneficial balance between mobility and stability, could be inserted minimally invasively.

SUMMARY

The present invention overcomes the disadvantages and deficiencies of the prior art. The present invention provides a spinal implant having a first expanded configuration, a first curved configuration, a second radially compressed configuration, and a second delivery configuration. The implant has a smaller transverse cross-sectional dimension in the radially compressed configuration than in the first expanded configuration and has a more linear configuration in the second delivery configuration than in the first curved configuration. The implant assumes the second radially compressed configuration and second delivery configuration during delivery to the disc space and assumes the first curved configuration and first expanded configuration upon placement within the disc space. The implant further moves towards the radially compressed configuration once implanted in response to a load placed on the implant by the vertebral bodies.

In a preferred embodiment, the implant is composed of shape memory material with a memorized position in the first expanded configuration and the first curved configuration. In one embodiment, the implant is C-shaped in the first curved configuration. In an alternate embodiment the implant forms a closed curve in the first curved configuration.

Several different cross-sectional configurations of the implant are disclosed including substantially C-shaped, substantially circular, and substantially rectangular having at least a first and second substantially planar surface.

The implant may include an insert made of a variety of materials such as elastic, viscoelastic or porous material. In one embodiment, the insert is contained by a tongue and groove arrangement.

The present invention also provides a spinal implant having an outer housing composed of shape memory material. The housing has a memorized non-linear configuration and is radially compressible from a first configuration to a second configuration by the vertebral bodies in response to a load placed on the housing and returns to its first configuration upon removal of the load. A filler material can be disposed within the outer housing.

The implant may contain a roughened surface on its outer surface to enhance bone ingrowth.

A method of minimally invasively inserting a spinal implant in a disc space is also provided. The method comprises:

providing a delivery instrument containing the spinal implant in a first configuration;

inserting the delivery instrument through a cannula to the disc space;

deploying the implant from the delivery instrument to position the implant in the disc space, the implant returning towards a memorized second configuration within the disc space; and removing the delivery instrument and leaving the implant in place, the implant moving between unstressed and stressed positions within the disc space in response to a load placed on the implant.

The method may further comprise the step of distracting the disc space with an inflatable balloon prior to deploying the implant from the delivery instrument. The method may also comprise the step of injecting cold saline into the delivery instrument to maintain the spinal implant in the martensitic state prior to deploying the implant, wherein the implant returns to the austenitic state in response to warming by body temperature when deployed from the delivery instrument. The method may further comprise the step of removing the disc nucleus through the cannula prior to the step of inserting the delivery instrument through the cannula.

BRIEF DESCRIPTION OF THE DRAWINGS

Preferred embodiment(s) of the present disclosure are described herein with reference to the drawings wherein:

FIG. 1 is a perspective view of a disc removal device being used in the intra-vertebral space through a cannula (the soft tissues are not shown);

FIG. 1a is a close up top view of the spinal disc nucleus being removed by the device of FIG. 1;

FIG. 2 is a perspective view of an implant delivery device being used in the intra-vertebral space (the soft tissues are not shown);

FIG. 2a is a close up top view of a spinal implant of the present invention being delivered from the device of FIG. 2;

FIG. 3 is a perspective view of an alternate embodiment of the delivery device being used in the intra-vertebral space having an integral angioplasty style balloon (the cannula is removed for clarity);

FIG. 3a is a close up top view of the delivery device of FIG. 3 showing the balloon inflated to distract the vertebral bodies;

FIG. 4 is a view similar to FIG. 3 except showing initial actuation of the handle to deliver the spinal implant;

FIG. 4a is a close up view showing the balloon inflated to maintain the space between vertebral bodies and the implant being delivered from the device;

FIG. 5 illustrates the delivery device of FIG. 2 being removed from the spine (the soft tissues are not shown) after implantation of the spinal implant;

FIG. 5a is a close up top view of the implant of FIG. 2a in place between the vertebral bodies;

FIG. 6 is a cross-sectional view of the spinal implant of FIG. 2a in its unstressed and unloaded condition between the vertebral bodies (the soft tissues are not shown);

FIG. 6a is a cross-sectional view of the spinal implant of FIG. 2a in an example of a stressed and loaded condition;

FIG. 7 is a perspective view of one embodiment of the implant of the present invention that is in a stressed condition (during delivery and when in use);

FIG. 7a illustrates the implant of FIG. 7 in an unstressed condition;

FIG. 7b is a cross-sectional view of an unfilled implant of the embodiment of FIG. 7 and FIG. 7a;

FIG. 7c is a cross-sectional view of a filled implant of the embodiment of FIGS. 7 and 7A;

FIGS. 7d and 7e are cross sectional views of alternate embodiments of the FIG. 7 implant;

FIG. 8 is a perspective view of another alternate embodiment of the implant that is in a stressed condition (during delivery and when in use);

FIG. 8a illustrates the implant of FIG. 8 in an unstressed condition;

FIG. 8b is a cross-sectional view of an unfilled implant of the embodiments of FIG. 8;

FIG. 8c is a cross-sectional view of a filled implant of the embodiment of FIG. 8;

FIG. 8d is a cross sectional view of an alternate embodiment of the FIG. 8 implant;

FIG. 8e is a cross-sectional view of the implant of FIG. 8;

FIG. 9 is a perspective view of another alternate embodiment of the implant that is in a stressed condition (during delivery and when in use);

FIG. 9a illustrates the implant of FIG. 9 in an unstressed condition;

FIG. 9b is a cross-sectional view of an unfilled alternate embodiment of the implant of FIG. 9;

FIG. 9c is a cross-sectional view of a filled alternate embodiment of the implant of FIG. 9;

FIG. 9d is a cross-sectional view of the implant of FIG. 9;

FIG. 9e is a cross-sectional view of an alternate embodiment of the FIG. 9 implant;

FIG. 10 is a perspective view of yet another alternate embodiment of the implant of the present invention that is in a stressed condition (during delivery and when in use);

FIG. 10a illustrates the implant of FIG. 10 in an unstressed condition;

FIGS. 10b and 10c are cross-sectional views of filled and unfilled implants of alternate embodiments of FIG. 10;

FIG. 10d is a cross-sectional view of the implant of FIG. 10;

FIG. 10e is a cross-sectional view of an alternate embodiment of the implant of FIG. 10;

FIG. 11 is a perspective view of another alternate embodiment of the implant of the present invention that is in a stressed condition (during delivery and when in use);

FIG. 11a illustrates the implant of FIG. 11 in an unstressed condition;

FIG. 11b is a cross sectional view of an unfilled embodiment of the implant of FIG. 11;

FIG. 11c is a cross-sectional view of the implant of FIG. 11;

FIGS. 11d and 11e are cross-sectional views of alternate embodiments of the implant of FIG. 11;

FIG. 12 is a perspective view of yet another alternate embodiment of the implant of the present invention that is in a stressed condition (during delivery and when in use);

FIG. 12a illustrates the implant of FIG. 12 in an unstressed condition;

FIG. 12b is a cross-sectional view of the implant of FIG. 12;

FIG. 12c is a cross-sectional view of a filled implant embodiment of the implant of FIG. 12;

FIGS. 12d and 12e are cross-sectional views of two alternate embodiments of the implant of FIG. 12;

FIG. 13 is a perspective view of an alternate embodiment of the implant having radial slits to increase flexibility;

FIG. 14 is a top view of the implant of FIG. 13 in the arcuate memorized configuration; and FIG. 15 is a perspective view of another alternate embodiment of the implant having a lattice structure.

DETAILED DESCRIPTION OF PREFERRED EMBODIMENTS

Referring now in detail to the drawings where like reference numerals identify similar or like components throughout the several views, several different embodiments of the spinal implant of the present invention are described herein. The spinal implants have differing cross-sectional configurations and can optionally contain an insert material to fill the void in the otherwise hollow implant and to provide more cushioning if desired. Each of these variations is described in detail below.

The spinal implants of the present invention are designed to be inserted minimally invasively into the disc space, thus enabling a smaller incision to be used in the procedure. This is achieved by the implants being compressible radially to a smaller diameter/height for delivery and being deflectable laterally to a substantially linear configuration. Once ejected from the delivery instrument at the desired site, i.e. the disc space between adjacent vertebrae, the implant returns to a larger diameter/height and to a curved configuration. Implanted in the disc space, the spinal implant is radially compressible in response to vertebral loads placed thereon, but attempts to return to its normal non-compressed (radially larger) configuration, thus providing a spring-like action.

Turning first to the instrumentation for minimally invasively preparing the disc space and for minimally invasively delivering the spinal implant, and with initial reference to FIGS. 1 and 1A, a device used in the intra-vertebral space to remove the spinal disc nucleus in a minimally invasive fashion is illustrated. The disc removal device 10 has an elongated tubular portion 12 which is inserted through an arthroscopic cannula 14 and has a pair of cutting jaws 16 which are operatively connected to and remotely manipulated, i.e. opened and closed, by proximal handle 18 to cut and remove the disc nucleus. Insertion through arthroscopic cannula 14 enables the disc to be removed minimally invasively rather than through a larger incision during an open more invasive surgical procedure.

As the nucleus is removed endoscopically, i.e. through a cannula forming a small incision, the implant of the present invention that is designed to replace the removed disc is also advantageously inserted minimally invasively. The instrument of FIG. 2, designated generally by reference numeral 20, contains the spinal implant 30 within a distal portion of the elongated tubular member 22. The instrument is inserted through cannula 14.

The implant delivery device 20 has a pusher 24 that is operatively connected to trigger 26 such that actuation of the trigger 26 moves pusher 24 longitudinally distally to advance the implant 30 from the tubular member 22. FIG. 2A illustrates the implant 30 partially ejected from device 20; FIG. 5A illustrates the implant 30 fully deployed and implanted in the disc space. After placement of the implant 30, the delivery device 20 is removed from the body as shown in FIG. 5.

As can be appreciated in the plan view of FIG. 5a and the cross-sectional views of FIGS. 6 and 6a, the implant is C-shaped in configuration as it extends circumferentially along the periphery of the disc space thus providing support along the periphery or circumference of the disc space. The first and second end portions 30a, 30b, are axially spaced and angled with respect to a longitudinal axis L of the intermediate portion 30c and extend towards each other. It is also contemplated that the implant could be a closed loop, e.g. circular, or extend more than 360 degrees so the end portions overlap. In each of these instances, the implant would be delivered in a substantially straighter configuration and would return to its memorized curved shape upon delivery to the disc space.

The implant 30 can have a variety of closed and open cross-sectional configurations. Exemplary embodiments of such implants of the present invention are shown in FIGS. 7-15. Each of the implants of FIGS. 7-15 are preferably composed of shape memory material which enables the implant to assume a second substantially straightened configuration as well as a second radially smaller configuration for delivery to the surgical site and return to a memorized first curved configuration and first radially larger (expanded) configuration for positioning at the disc space. Once delivered to the disc space, the memory characteristics of the implant provide sufficient springiness in response to vertebral loads placed on the device by the spine. That is, the implant can move between an unstressed and stressed position in response to a load placed on the implant, but returns to (or toward) its original unstressed position upon release of the load. This provides both support for the vertebral bodies plus the desired flexibility. One preferable shape memory material is Nitinol, a nickel titanium alloy, although other shape memory metals or polymeric materials are contemplated.

It should be appreciated that the alternate embodiments of FIGS. 7-15 which show different configurations of the implant illustrate the implant in a linear configuration for simplicity, it being understood that the implant would be formed into a memorized open or closed curve configuration. The length of the implant could also be longer than that shown in the drawings for assuming the curved shape.

The implant 30 can be hollow or alternatively can form a support or outer housing for a filler material. The insert (filler) material can fill the void in the implant to provide a more cushioning or a more spring-like effect. This "squeezable" insert (filler) can be made of an elastic material such as rubber to provide additional springiness, a viscoelastic material such as menisci and advanced polymers which would compress and more slowly return to its non-compressed state or a porous viscoelastic material such as articular cartilage which will enable exit of fluids through the pores. The insert material can also be resorbable.

The compressed or reduced cross-section condition of the shape memory implant can be achieved by containment within the delivery tube as the inner walls apply stress to the implant. Alternatively, cool saline or other fluid can be injected through the tubular portion of the instrument 20 during delivery of the implant to maintain the implant in the cooler softer martensitic state to facilitate ejection. Once the implant is advanced from the delivery instrument 20, the warmer body temperature will transform the implant to the austenitic memorized condition corresponding to an arcuate shape and larger cross-sectional dimension. The implant has a first cross-sectional transverse dimension measured from the upper surface to the lower surface in the compressed configuration and a second transverse cross-sectional dimension upon delivery from the instrument. The second transverse dimension is measured from the upper surface to the lower surface in the second configuration of the implant and the second transverse dimension is greater than the first cross sectional transverse dimension. The upper and lower surfaces are joined by a side wall.

Turning first to the embodiment of FIG. 7, implant 40 is circular in transverse cross-section and has an overlapping edge 42. In the delivery position of FIG. 7, the diameter of the implant 40 is smaller than the diameter in the unstressed implanted position of FIG. 7a. The implant 40 can contain a void 41 in the center or optionally include an insert/filler material 44 as described above to fill the interior of implant 40a. Both a hollow and a filled version are illustrated in FIGS. 7b and 7c respectfully. In the embodiments of FIGS. 7d and 7e, the filler (insert) material and implant cooperate in a tongue and groove arrangement to enhance retention of the filler material within the implant. A groove 45 can be provided in the insert 46 contained within implant 40b to receive tongue 48 (FIG. 7d) or alternatively a groove 47 can be provided in the implant 40c (FIG. 7e).

In the alternate embodiment of FIG. 8, the overlapping portions of the implant 50 are spaced apart, creating a gap 53 by overlapping edge 52. The implant (50a), including the gap can be filled with insert material 54 (FIG. 8c) or alternatively be devoid of such material as in implant 50b of FIG. 8b. FIG. 8d shows the tongue and groove arrangement, similar to FIG. 7d, with the groove 55 for receiving tongue 57 being provided in the insert 56 of implant 50c. A groove 58 can alternatively be provided in the implant 50 to receive tongue 59 of insert 51 (see FIGS. 8a and 8e).

In the alternate embodiment of FIG. 9, the implant 60 has a closed loop, i.e. a circular, transverse cross-sectional configuration. The implant can be hollow (see implant 60a of FIG. 9b) or alternatively can be filled with insert material 64 (see implant 60b of FIG. 9c). FIG. 9d shows the tongue and groove arrangement, similar to FIG. 7c, of implant 60d with the groove 65 being provided in the insert 66 to receive tongue 67. Alternatively, the groove can be provided in the implant such as groove 68 provided in the implant 60c of FIG. 9e.

In FIG. 10, implant 70 has an open loop configuration providing a C-shape transverse cross-section. The implant can be hollow (see implant 70a of FIG. 10b) or can include an insert material 74 (implant 70b of FIG. 10c). Tongue and groove arrangements are illustrated in the cross-sectional views of FIGS. 10d and 10e, with FIG. 10d reflecting the implant 70 of FIG. 10 having groove 75 formed in insert material 76 and FIG. 10e showing an alternate embodiment with the tongue 77 on insert material 78 of implant 70c.

In FIG. 11, a C-shaped cross-sectional implant 80 is illustrated. This implant 80 resembles implant 70 of FIG. 10 in that it has an open curved configuration. It differs from the embodiments of FIG. 10, however, in that it is more oval in cross-section. As with the previous embodiments, insert material 84 can be provided as well as tongue and groove arrangements (85, 87 and 88, 89 in implants 80b and 80c, respectively) as shown in FIGS. 11d and 11e. FIG. 11b illustrates implant 80a devoid of filler material.

In the embodiment of FIG. 12, a C-shaped implant 90 is also illustrated, except that it is more in the form of an open rectangle in cross-section. Planar surfaces 91, 92 increase the contact area with the vertebral bodies. Insert material 94 can optionally be provided in implant 90a as shown in FIG. 12c. Alternative tongue and groove arrangements are illustrated in the cross-sectional views of FIGS. 12d and 12e, with the groove 95 of implant 90b provided on insert material 96 to receive tongue 98 (FIG. 12d) and the groove 99 being provided on implant 90c to receive tongue 97 (FIG. 12e).

FIGS. 13-15 illustrate alternative embodiments of the implant to increase flexibility during delivery and during compression once inserted. In FIG. 13, implant 100 has a series of fenestrations 102 along its length. Narrower slits can alternatively be provided. Although shown extending in an orientation transverse to the disc space (longitudinally aligned with the spine) the fenestrations can alternatively be angled. The circumferential slits or openings can be spaced further apart or closer together and can extend for differing degrees around the circumference. When in the memorized curved configuration upon implantation, the slits spread to form wider gaps as shown in the top of view of the implant of FIG. 14. A lattice structure 118 is illustrated in FIG. 15, also to provide increased flexibility. Filler material can be provided in each of these inserts.

Any of the foregoing implants can be provided with a roughened surface, such as a textured surface, to enhance bone ingrowth to enhance implant retention in the disc space. Surface finishes such as hydroxyapatite, calcium silicate and calcium phosphate could also be applied to allow for bone ingrowth.

In use, the disc nucleus is removed arthroscopically, i.e. through cannula 14, by device 10. Cannula 14 can optionally be placed by first inserting a needle and wire, removing the needle and sequentially placing and removing dilators of progressively increasing diameter over the wire until the desired cannula diameter is reached. After removal of the disc, device 10 is withdrawn through cannula 14 and then delivery device 20, containing any of the foregoing implants, is inserted through the cannula. The implant is contained within the delivery device 20 in a substantially straightened configuration and in a reduced diameter (compressed/stressed) configuration, either by the walls of the device or by injection of cold saline to transform the implant to the martensitic state as described above. The implant is then ejected from the tubular member 22 of the delivery device 20 and implanted in the disc space between the vertebral bodies. The delivery instrument 20 and cannula 14 are withdrawn from the body. FIGS. 6 and 6a illustrate the implant 30 positioned within the disc space in an unstressed position (FIG. 6) and an example of a stressed position (FIG. 6a) to illustrate the compressibility of the implant in response to vertebral loads. When the load is released, the implant returns to the unstressed position of FIG. 6 or at least to a less compressed configuration, depending on the gap between adjacent vertebrae. The degree of compressibility of the implant will depend on the applied load.

To facilitate insertion and enhance distraction of the disc space, a balloon can be provided as part of the implant delivery system. This is illustrated in FIGS. 3 and 4 (the cannula is not shown). The delivery instrument 120 has an elongated tubular portion 122 and a trigger 126 as in the embodiment of FIG. 1. An axial bore 128 is formed along the length of device 120 to receive catheter 132 having an inflatable balloon 134, such as an angioplasty balloon, at the distal end. The proximal end 136 of the catheter has an inflation portion for inflating the balloon 134 within the disc space as shown in FIG. 3a. This inflation aids to distract the vertebrae to facilitate insertion of the implant. After inflation, trigger 126 is squeezed in the direction of the arrow of FIG. 4 to eject the implant contained in the tubular portion 122 as shown in FIG. 4a. After implantation, the balloon 134 is deflated and instrument 120 and catheter 132 are withdrawn from the surgical site, leaving the implant in the disc space. It should be appreciated that the balloon catheter can be either an integral part of the delivery instrument or a separate device removably inserted through the bore of the delivery instrument.

While the above description contains many specifics, those specifics should not be construed as limitations on the scope of the disclosure, but merely as exemplifications of preferred embodiments thereof. For example, in addition to the substantially C-shaped, circular and rectangular cross-sectional configurations, substantially hexagonal, substantially octagonal as well as other configurations are contemplated. Those skilled in the art will envision many other possible variations that are within the scope and spirit of the disclosure as defined by the claims appended hereto.

What is claimed is:

1. A method of minimally invasively inserting a spinal implant in a disc space comprising:
   providing a delivery instrument containing the spinal implant in a first configuration;
   inserting the delivery instrument through a cannula to the disc space, the delivery instrument including a pusher to contact the spinal implant;
   deploying the implant from the delivery instrument to position the implant in the disc space at a desired implant location, the implant composed of a shape memory material and being in a first substantially linear elongated configuration and a compressed configuration in the delivery instrument for delivery and a second curved and shape memorized expanded configuration when deployed from the delivery instrument to fill a height of the disc space, the implant returning towards the shape memorized configuration and curved configuration within the disc space when deployed from the delivery instrument and fully contained within the disc space in a desired position within the disc space upon delivery from the delivery instrument, the implant having an upper surface and a lower surface joined by a side wall and a cushioning filler material between the upper and lower surfaces, wherein deploying the implant exposes the implant from the delivery instrument so that the implant moves from the compressed configuration toward the memorized position, the implant having a first cross-sectional transverse dimension measured from the upper surface to the lower surface in the compressed configuration and a second transverse cross-sectional dimension upon delivery from the instrument, the second transverse dimension measured from the upper surface to the lower surface in the second configuration which is greater than the first cross sectional transverse dimension; and
   removing the entire delivery instrument including the pusher completely from a body of the patient after delivery of the implant and leaving the implant in place along a periphery of the disc space, the delivered implant spaced from a center of the disc space and extending circumferentially along the periphery of the disc space, the implant moving between unstressed and stressed positions within the disc space, with the filler material providing additional springiness, in response to a load placed on the implant, the cross-sectional transverse dimension of the implant varying as the load is placed on the implant in its shaped memorized expanded configuration within the disc space.

2. The method of claim 1, further comprising the step of distracting the disc space with an inflatable balloon prior to deploying the implant from the delivery instrument.

3. The method of claim 1, further comprising the step of injecting cold saline into the delivery instrument to maintain the spinal implant in the martensitic state prior to deploying the implant, the implant returning to the austenitic state in response to warming by body temperature when deployed from the delivery instrument.

4. The method of claim 1, further comprising the step removing the disc nucleus through the cannula prior to the step of inserting the delivery instrument through the cannula.

5. The method of claim 1, wherein the step of deploying the implant further includes exposing the implant so that the first and second ends of the implant move from a first position where they are in substantial axial alignment to a second position where they curve toward each other, the first and second ends being non-overlapping and closer to each other in the shape memorized configuration than in the compressed configuration.

6. The method of claim 5, wherein the step of deploying the implant causes the implant to assume a C-shaped configuration with the C-shape extending circumferentially along the periphery of the disc space.

7. The method of claim 1, wherein as the implant moves between stressed and unstressed positions, the upper and lower surfaces respectively move toward and away from each other.

8. The method of claim 7, wherein the implant maintains a C-shaped configuration as the implant moves between the stressed and unstressed positions.

9. The method of claim 1, wherein the step of providing a delivery instrument containing the spinal implant includes the step of providing an implant with a support having a void therein and the filler material positioned within the void, wherein movement of the implant from the unstressed to the stressed position compresses the filler material.

10. The method of claim 1, wherein the shape memory material of the implant directly contacts tissue in the disc space.

11. The method of claim 1, wherein the implant and the filler material cooperate with a tongue and groove arrangement.

12. The method of claim 1, wherein the implant extends almost along an entire periphery of the disc space.

* * * * *